United States Patent [19]
Nishimura et al.

[11] Patent Number: 5,935,825
[45] Date of Patent: Aug. 10, 1999

[54] PROCESS AND REAGENT FOR AMPLIFYING NUCLEIC ACID SEQUENCES

[75] Inventors: Naoyuki Nishimura, Kyoto; Tomoko Nakayama, Osaka, both of Japan

[73] Assignee: Shimadzu Corporation, Kyoto, Japan

[21] Appl. No.: 08/345,393

[22] Filed: Nov. 18, 1994

[51] Int. Cl.$^6$ ............... C12P 19/34; C12Q 1/68; C12N 1/08; C07H 21/04
[52] U.S. Cl. .......... 435/91.2; 435/6; 435/91.1; 435/270; 435/810; 536/23.1; 536/24.33; 536/25.3
[58] Field of Search ............ 435/5, 6, 91.1, 435/91.2, 183, 810, 974, 270; 536/23.1, 23.2, 23.72, 24.3, 24.32, 24.33, 25.3; 935/1, 5, 8, 76, 77, 78

[56] References Cited

U.S. PATENT DOCUMENTS

| | | | |
|---|---|---|---|
| 4,800,159 | 1/1989 | Mullis et al. | 435/172.3 |
| 4,983,511 | 1/1991 | Geiger et al. | 435/6 |
| 5,213,796 | 5/1993 | Garcea et al. | 424/89 |
| 5,221,610 | 6/1993 | Montagnier et al. | 435/7.1 |
| 5,234,809 | 8/1993 | Boom et al. | 435/91 |
| 5,364,790 | 11/1994 | Atwood et al. | 435/288 |
| 5,420,029 | 5/1995 | Gelfand et al. | 435/194 |
| 5,436,144 | 7/1995 | Stewart et al. | 435/91.2 |
| 5,501,963 | 3/1996 | Burckhardt | 435/91.2 |
| 5,527,510 | 6/1996 | Atwood et al. | 422/104 |
| 5,629,158 | 5/1997 | Uhlen | 435/6 |

FOREIGN PATENT DOCUMENTS

| | | | |
|---|---|---|---|
| 90/02821 | 3/1990 | WIPO | C12Q 1/70 |

OTHER PUBLICATIONS

Boehringer Mannheim Biochemicals Catalog 1990/91, pp. 63–64.

Casareale et al., "Improved Blood Sample Processing for PCR," PCR Methods and Applications, pp. 149–153, 1992.

Fluka Catalog 1988/89, pp. 1304–1305.

*Primary Examiner*—Bradley L. Sisson
*Attorney, Agent, or Firm*—Nikaido Marmelstein Murray & Oram, LLP

[57] ABSTRACT

This invention is directed to a novel method for PCR amplification wherein PCR is carried out at a higher pH than the pH widely used in the art. Specifically, the buffer solution is adjusted to pH 9.0 to 11.0 at 25° C. Using the present invention, DNA amplification can be successfully carried out following a simple pretreatment. In the present invention whole blood is mixed with a hypotonic solution so that a selective lysis of red blood cells takes place. The residual leukocytes are then collected. The leukocytes are mixed with a polymerization agent, primers and other necessary reagents and PCR is carried out. When the PCR solution is placed at a high temperature for DNA denaturation, the leukocytes are lysed so that the leukocyte DNA is released and can access the primers and the other necessary reactions for PCR in the solution.

Cell membranes and proteins are present in the PCR reaction solution due to the lack of a protein extractive step during the pretreatment. Nevertheless DNA amplification occurs under the presently claimed improved PCR method.

22 Claims, 1 Drawing Sheet

```
                       SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 20 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

GCACAGCTGT GTTTACTAGC

20

(2) INFORMATION FOR SEQ ID NO:2:

(i) SEQUENCE CHARACTERISTICS:
        (A) LENGTH: 20 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CACATACCTC CTTCCACTCG

20
```

PROCESS AND REAGENT FOR AMPLIFYING NUCLEIC ACID SEQUENCES

BACKGROUND OF THE INVENTION

(1) Field of the Invention

This invention relates to a method for amplifying DNA, and in particular to an improved method for amplifying DNA by Polymerase Chain Reaction (PCR).

(2) Description of the Related Art

The PCR is an In vitro method for the enzymatic synthesis of specific DNA sequences, using two oligonucleotide primers that hybridize to opposite strands and flank the region of interest in the target DNA. PCR is described in U.S. Pat. Nos. 4,683,195 and 4,683,202 by K. B. Mullis et al.

The PCR is a highly sensitive test for the detection of DNA in blood, especially in peripheral blood leukocytes. Thus, PCR is a potentially powerful tool for use in the diagnosis of infectious diseases caused by microorganisms, hereditary diseases, cancers, etc. In addition, PCR is particularly suitable for determining parent/child relationships as peripheral blood is frequently the specimen of choice in such a determination.

One disadvantage to using PCR is that impurities such as pigmentary compounds, proteins, sugars and unidentified compounds inhibit the reaction. Therefore, separation of the cells from materials and the subsequent extraction of DNA from the cells is necessary prior to amplification by PCR. In order to overcome this inhibition, cellular lysis can be accomplished with enzymes, detergents or chaotropic agents and traditionally, the subsequent extraction of the nucleic acid from the cellular lysate has involved using phenol or phenol-chloroform mixture. More recent methods of purifying the DNA include the removal of impurities by using ion exchange resins, glass filter or beads or agents for protein flocculation.

One method (and reagent kit) for removing impurities is commercially marketed under the name of "COLLECTAGENE" (AMRAD Operations Pty Ltd., Victoria, Australia). In this method, the sample is prepared as follows:

1. Anticoagulant-treated whole blood of mammalian origin is mixed with Magnetic Particles in a tube, whereby the leukocyte cells and the Magnetic Particles are conjugated.

2. The conjugated cells and Magnetic Particles are washed with phosphate buffer.

3. The conjugated cells are lysed with proteinase whereby the proteins are degraded and the DNA in the leukocyte cells is released.

4. The tube is then heated to inactivate the residual proteinase resulting in a solution of free leukocyte DNA which is ready for PCR.

Meanwhile, RNA-PCR is utilized for detecting and/or sequencing target RNA and thus has potential for use as diagnostic tests and medical or environmental analyses. For example RNA-PCR may be useful for detecting HCV (hepatitis C virus) which causes hepatitis, and HIV (human immunodeficiency virus) which causes AIDS.

During RNA-PCR, a DNA which has a complementary base structure, (cDNA), is first synthesized using the target RNA as a template in the presence of reverse transcriptase. Then the cDNA is amplified by PCR. Under current technology, when treating the RNA obtained from living organisms (in particular from blood), purification of the RNA is necessary. Basically, the RNA can be purified using the same as the purification method for DNA.

In both DNA and RNA purifications it is difficult to sufficiently remove the impurities and thus the succeeding DNA amplification frequently ends in failure, especially when the sample contains a few copies of DNA. In addition, the purification methods are lengthy, complex, and costly.

Although, improved DNA purification methods such as the "COLLECTAGENE" method described above, are shorter and simpler to remove impurities, however, the possibility of contaminating DNA still remains. Because PCR methods are so sensitive that one DNA molecule in the specimen can be amplified, contamination may cause serious problems. Therefore, a simpler pretreatment which has less possibility of contamination is desirable.

In addition, a simpler method is desirable especially, for everyday use in the clinical field.

The present invention addresses these and other problems associated with PCR amplification procedures and is believed to represent a significant advance in the art.

The object of the present invention is to provide a PCR method which can achieve a specific amplification in the presence of impurities.

Another object of the present invention is to provide a PCR method suitable for everyday use in the clinical field.

Another object of the present invention is to provide a suitable kit for PCR, particularly a kit for use with blood samples.

Another object of the present invention is to provide diagnostic methods for detecting HIV (human immunodeficiency virus) which causes AIDS, HCV (hepatitis C virus) or HBV (hepatitis B virus) which cause hepatitis, a septicemia causative bacteria, cancer or hereditary diseases, using PCR or RNA-PCR.

More particularly, the object of this invention is to provide an improved process of PCR for DNA contained in leukocytes in peripheral blood.

SUMMARY OF THE INVENTION

This invention is directed to novel methods for PCR wherein PCR is carried out at a higher pH than the pH widely used in prior art processes. In particular, the pH buffering solution which is one of the reagents used in various PCR methods, is adjusted to a pH between 9.0 and 11.0.

According to the present invention, specific DNA amplification is successfully carried out after a rather simple pretreatment. In the present invention, whole blood is mixed with a hypotonic solution so that a selective lysis of red blood cells takes place. Then, the residual leukocytes are collected. The intact leukocytes are mixed with a polymerization agent, primers and other necessary reagents and the PCR cycle takes place. During the process, when the PCR solution is placed under high temperature for denaturation of the DNA, the leukocytes are lysed so that the leukocyte DNA is released and can access the primers and the other necessary reagents for PCR in the solution.

Cell membranes, proteins and other impurities are present during the PCR reaction due to the lack of a protein extractive step. Despite the presence of these impurities, DNA amplification occurs under the present, improved PCR method.

The preferred buffer for use in the present invention consists of Tris (hydroxymethyl) aminomethane and a mineral acid, usually hydrochloric acid. The tris buffer, which has a pH between 9.0 and 11.0 when measured at 25° C., is used in a concentration of 10 mM to 100 mM in the PCR reaction solution.

General reaction conditions and variations of the polymerase chain reaction are disclosed in U.S. Pat. Nos. 4,683,195 and 4,683,202 the disclosures of which are herein incorporated by reference into the present application.

DESCRIPTION OF THE PREFERRED EMBODIMENTS

Figure 1A:
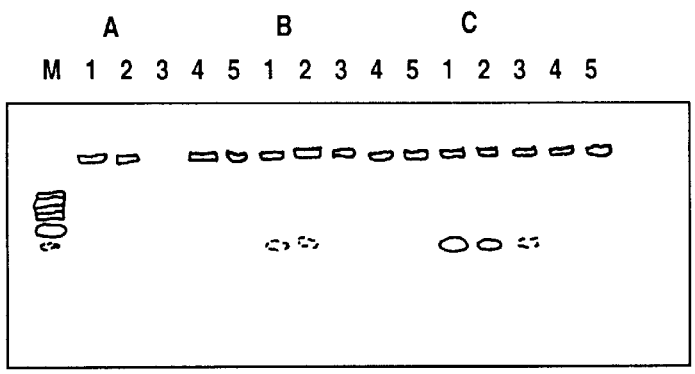
FIGS. 1a and 1b shows the results of the PCR in Example 1 by agarose gel electrophoresis, wherein the PCR was carried out with Tris buffers of varying pH and different concentrations of the target DNA.

The term "primer" as used in the present application, refers to an oligonucleotide which is capable of acting as a point of initiation of synthesis in the presence of nucleotide and a polymerization agent. The primers are preferably single stranded but may be double stranded. If the primers are double stranded, the strands are separated prior to the amplification reaction. The primers used in the present invention, are selected so that they are sufficiently complementary to the different strands of the sequence to be amplified that the primers are able to hybridize to the strands of the sequence under the amplification reaction conditions. Thus, noncomplementary bases or sequences can be included in the primers provided that the primers are sufficiently complementary to the sequence of interest to hybridize to the sequence.

The oligonucleotide primers can be prepared by methods which are well known in the art or can be isolated from a biological source. One method for synthesizing oligonucleotide primers on a solid support is disclosed in U.S. Pat. No. 4,458,068 the disclosure of which is herein incorporated by reference into the present application.

The term "nucleic acid" as used in the present application refers to double or single stranded DNA or RNA or a double stranded DNA-RNA hybrid. The nucleic acids may be obtained from any source but are preferably obtained from blood or other tissues such as chorionic villi or amniotic cells. Any nucleic acid can be amplified using the present invention as long as a sufficient number of bases at both ends of the sequence are known so that oligonucleotide primers can be prepared which will hybridize to different strands of the sequence to be amplified.

The term "deoxyribonucleoside triphosphates" refers to dATP, dCTP, dGTP, and dTTP.

The term "polymerization agent" as used in the present application refers to any compound or system which can be used to synthesize a primer extension product. Suitable compounds include but are not limited to E. coli DNA polymerase I, Klenow fragment of E. coli DNA polymerase I, T4 DNA polymerase, T. litoralis DNA polymerase, Taq polymerase and reverse transcriptase.

The term "thermostable" as used in the present application refers to a substance which retains activity at an elevated temperature, preferably 65–90° C.

The following examples illustrate the present invention but are not intended to limit the invention in any manner.

EXAMPLE 1

PCR was carried out with Tris buffers of varying pH which were added to a PCR solution in order to maintain the pH of the solution within a certain range throughout the reaction cycle.

The target DNA sequence to be amplified was a 174 base pair sequence contained within the mouse beta-globin gene. The following two oligodeoxyribonucleotide primers were prepared using conventional techniques.

P1:  5'GCACAGCTGTGTTTACTAGC3'   (SEQ ID NO:1)

P2:  5'CACATACCTCCTTCCACTCG3'   (SEQ ID NO:2)

The P1 primer is homologous to the plus-strand and the P2 primer is homologous to the minus strand of the target sequence.

By adding mouse blood to normal human blood, the present inventors designed a model system of virus infected human blood where the DNA of mouse origin was a model for integrated DNA, such as a DNA fragment incorporated by a virus.

Whole blood from a Balb/c mouse was diluted step-wise with phosphate buffer saline (2.68 mM KCl, 1.47 mM $KH_2PO_4$, 137 mM NaCl, 8.1 mM $Na_2HPO_4$), to obtain solutions which contain $10^4$, $10^3$, $10^2$, 10, and 0 leukocytes in a 2 µl solution.

27 µl of sodium citrate treated whole blood of normal human origin, which contained 5,100 leukocytes in 1 µl, was placed into 0.5 ml micro-centrifuge tubes. 2 µl of the step-wise diluted solutions of mouse blood was added to the tubes, so that model human blood with different concentrations of the target DNA was obtained. The model blood contained either $10^4$, $10^3$, $10^2$, 10, or 0 mouse leukocytes respectively.

150 µl of a lysis solution (34 mM NaCl, 1 mM EDTA) was added to each tube and mixed well. After placing on ice for 1 minute so that the erythrocytes in the samples were lysed due to the reduced osmotic pressure, the tubes were centrifuged at 10,000 rpm for 1 min. at 4° C. The supernatant was then aspirated by a micropipette. The residual leukocyte pellet was subjected to an amplification reaction.

In order to examine the relationship between pH and the degree of DNA amplification, several reaction solutions which differed only in the pH of the Tris buffer were prepared.

Tris was first dissolved in distilled water to make a one molar solution. The solution was divided into 6 parts. HCl was dropped into each solution to adjust the pH values of the solutions to 8.3, 9.0, 9.5, 10.0, 10.5, and 11.0 respectively. The various Tris solutions were then used to prepare the reaction mixture.

Reaction Mixture for PCR 10 mM Tris buffer: one of the six 1 M Tris buffers described above was added to adjust the final concentration of Tris to 10 mM 1 µM each of primers P1 and P2

1.5 mM $MgCl_2$ 50 mM KCl

200 µM of each deoxyribonucleotide (dNTP):i.e., deoxy-adenosine-triphosphate(dATP), deoxy-guanosine-triphosphate(dGTP), deoxy-thymidine-triphosphate (dTTP) and deoxy-cytidine-triphosphate(dCTP)

2.5 units of Taq DNA polymerase (provided by Perkin-Elmer Cetus Instruments under the name of "Ampli Taq")

100 µl of the reaction mixture for PCR was added to the leukocyte pellets in the tubes. 75 µl of mineral oil was overlaid on the solution in the tubes.

The tubes were incubated at 94° C. for 1.5 minutes, whereby DNA release and denaturation took place.

40 cycles of PCR using the following temperature profile were performed:

| Denaturation | 94° C., 1 minute |
| Primer Annealing | 55° C., 1 minute |
| Primer Extension | 72° C., 1 minute |

The PCR cycles were concluded with a final extension at 72° C. for 7 minutes.

Agarose gel electrophoresis was employed to detect the amplified DNA. 10 μl of each DNA solution obtained after the thermal cycling, was applied to a 3% agarose gel and separated by electrophoresis at 3 to 4 Vcm$^{-1}$ for 40 minutes in TAE buffer (40 mM Tris-acetate 1 mM EDTA, pH 8.0). A 0.5 μg/ml ethidium bromide solution was used as a fluorescent dye to detect the DNA bands.

According to the prior art, Tris (hydroxymethyl) aminomethane is a dipolar ionic buffer having a $pK_a$ of 8.3 at 20° C., and a Δ $pK_a$ of −0.021. Thus the pH value of the reaction solution during thermal cycling should be lower than the pH measured at 25° C.

In order to determine the actual pH during PCR thermal cycling, the pH of the reaction solution was measured at various temperatures. Specifically, the above mentioned reaction mixture for PCR (the mixture of Tris buffer, primers, dNTP etc.) was placed at 25° C., 55° C. and 70° C. in an incubator and the pH was measured with a pH meter.

The following table shows the results of the measurement. pH of the reaction mixture at

| 1M Tris | 25° C. | 55° C. | 70° C. |
|---|---|---|---|
| 5.3 | 8.0 | 7.2 | 6.8 |
| 9.0 | 8.7 | 7.9 | 7.5 |
| 9.5 | 8.9 | 8.1 | 7.7 |
| 10.0 | 9.2 | 8.3 | 7.9 |
| 10.5 | 9.2 | 8.4 | 8.0 |
| 11.0 | 9.2 | 8.4 | 8.0 |

Figure 1B:
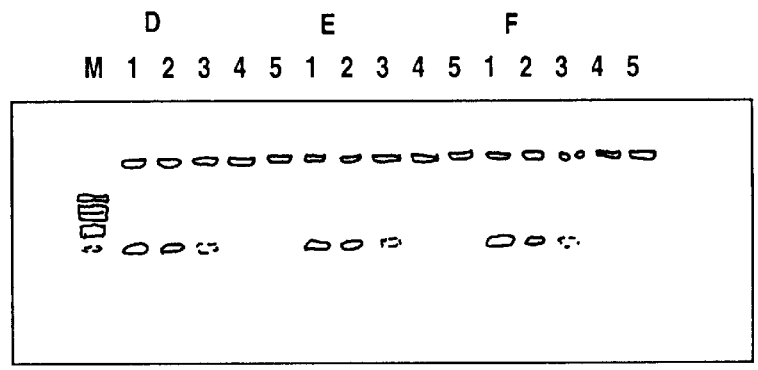

The results of Example 1 are shown in FIG. 1. In FIG. 1, the letters A to F represent 1 M Tris buffers of varying pH with which the PCR was carried out, namely:

| Letter | pH |
|---|---|
| A | 8.3 |
| B | 9.0 |
| C | 9.5 |
| D | 10.0 |
| E | 10.5 |
| F | 11.0 |

In FIG. 1, the numbers 1 to 5 represent different concentrations of the mouse leukocytes which included the target DNA fragment, namely:

| Number | Concentration of mouse leukocytes in the tube |
|---|---|
| 1 | $10^4$ |
| 2 | $10^3$ |
| 3 | $10^2$ |
| 4 | 10 |
| 5 | 0 |

The letter M represents a molecular weight marker which is Hinc II-digested φ×174 RF DNA.

In lanes A1, A2, A3, A4 and A5, there was no detectable DNA band. This means that when PCR was carried out with pH 8.3 buffer, even though the mixture contained $10^4$ leukocytes, no amplification occurred.

However, when PCR was carried out with pH 9.0 buffer, amplified DNA was detected in lanes B1 and B2. Thus, the PCR amplification took place with a relatively high concentration of leukocytes, $10^4$ and $10^3$.

Amplified DNA band were also detected in lane 3 as well as lanes 1 and 2 of C, D, E and F respectively. This means that when PCR was carried out with buffers at pH 9.5, 10.0, 10.5 and 11.0, the amplification took place with a $10^2$ concentration of the leukocytes as well as with higher concentrations of the leukocytes.

EXAMPLE 2

In this assay, PCR was carried out with CHES buffers, 2-(Cyclohexylamino) ethanesulfonic acid, of varying pH and CAPSO buffer, 3-N-Cyclohexylamino-2-hydroxypropanesulfonic acid.

The target DNA was the same mouse gene fragment as used in Example 1. The model system of virus infected human blood was essentially the same as in Example 1 and was prepared as follows.

26.5 μl of sodium citrate treated whole blood of normal human origin which contained 5,200 leukocytes in 1 μl, was dispensed into micro-centrifuge tubes. 2 μl of step-wise diluted phosphate buffer solutions of mouse blood was added to the tubes to produce model human blood with varying concentrations of the target DNA. The model blood contained $10^4$, $10^3$, $10^2$, 10, or 0 mouse leukocytes respectively.

The pretreatment of the whole blood was the same as in Example 1. 150 μl of a lysis solution (34 mM NaCl, 1 mM EDTA) was added to each tube and mixed well. After placing on ice for 5 minutes so that the erythrocytes were lysed due to the reduced osmotic pressure, the tubes were centrifuged at 10,000 rpm for 1 minute at 4° C. The supernatant was then aspirated with a micropipette. The residual leukocyte pellet was subjected to DNA amplification.

The reaction solution for PCR was the same as in Example 1 with the exception of the pH buffer. Either CHES or CAPSO buffer was used as the pH buffer.

200 μM CHES buffers were prepared as follows. CHES was dissolved in distilled water to make a 200 millimolar solution. The solution was divided into 2 portions. Concentrated NaOH solution was dropped into each portion to adjust the pH to 8.3 and 9.0 respectively.

200 mM CAPSO buffer was prepared as follows. CAPSO was dissolved in distilled water to make a 200 millimolar solution. Concentrated NaOH solution was dropped into the solution to adjust the pH to 9.5.

Reaction Mixture for PCR 10 mM CHES buffer: one of the two 200 mM CHES buffers described above was added to produce a final concentration of 10 mM CHES or 10 mM CAPSO buffer: the 200 mM CAPSO buffer was added to produce a final concentration of 10 mM CAPSO 1 μM each of primers P1 and P2

1.5 mM $MgCl_2$ 50 mM KCl

200 μM each deoxyribonucleotide (dNTP):i.e., deoxy-adenosine-triphosphate(dATP), deoxy-guanosine-triphosphate(dGTP), deoxy-thymidine-triphosphate (dTTP) and deoxy-cytidine-triphosphate(dCTP)

2.5 units of Taq DNA polymerase (provided by Perkin-Elmer Cetus Instruments under the name of "Ampli Taq")

100 μl of the reaction mixture for PCR was added to the leukocyte pellets in the tubes. 75 μl of mineral oil was overlaid on the solution in the tubes.

The conditions for thermal cycling and detection by gel electrophoresis were the same as in Example 1.

According to the prior art, the pKa of CHES is 9.3 and the pKa of CAPSO is 10.0. The pH of the reaction solution at different temperatures was measured. The results were as follows:

|  | pH of the reaction mixture | | |
|---|---|---|---|
|  | 25° C. | 55° C. | 70° C. |
| 200 mM CHES | | | |
| 8.3 | 8.1 | 7.5 | 7.2 |
| 9.0 | 8.9 | 5.2 | 7.5 |
| 200 mM CAPSO | | | |
| 9.5 | 9.4 | 8.6 | 8.2 |

Figure 2:
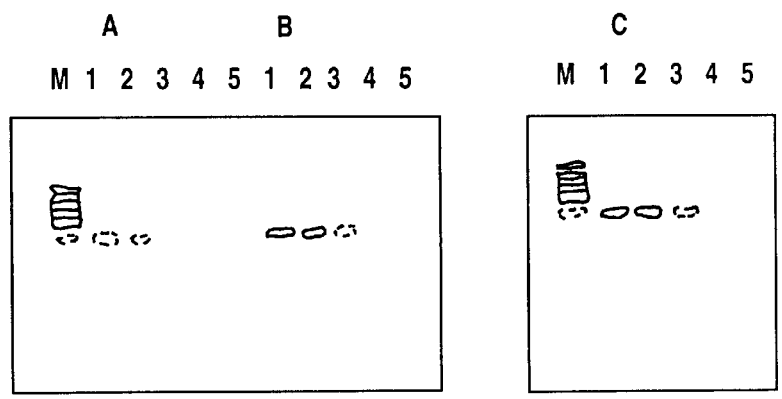
FIG. 2 shows the results of PCR in Example 2 by agarose gel electrophoresis, wherein the PCR was carried out with CHES and CAPSO buffers of varying pH and different concentrations of the target DNA.

The results of Example 2 are shown in FIG. 2. The letters A and B represent the 200 mM CHES buffers of pH 8.3 and 9.0 with which the PCR was carried out. The letter C represents the CAPSO buffer of pH 9.5. The numbers 1 to 5 represent the different concentrations of the mouse leukocytes as follows:

| FIG. | Number of mouse leukocytes in the tube |
|---|---|
| 1 | $10^4$ |
| 2 | $10^3$ |
| 3 | $10^2$ |
| 4 | 10 |
| 5 | 0 |

The letter M represents a molecular weight marker which is Hinc II-digested φx174 RF DNA.

When PCR was carried out with pH 8.3 CHES buffer, the amplified DNA was detected in lanes A1 and A2. When PCR was carried out with the pH 9.0 buffer, the amplified DNA was detected in lanes B1, B2 and B3. Thus, the higher pH produced a positive effect on DNA amplification.

There were also detectable DNA bands in lanes C1, C2 and C3. Thus, relatively low concentrations of DNA, $10^2$, can be amplified as well as relatively high concentrations of DNA, $10^4$ and $10^3$, when CAPSO buffer at pH 9.5 is used.

Thus, amplified DNA bands were detectable in lanes A1 and A2, which show the results of PCR carried out with CHES buffer at pH 8.3. As discussed above in Example 1, amplification did not take place when a Tris buffer at pH 8.3 was used after a simple pretreatment such as the one used in Examples 1 and 2. The initial pH of both the CHES and Tris buffers were the same. The only difference between the Tris and CHES buffers is the pH range at high temperatures (such as the temperature used during the thermal cycling). The 10 mM Tris buffer solution has a pH of 6.8 at 70° C. However, the 10 mM CHES buffer solution has a pH of 7.2 at 70° C.

EXAMPLE 3

The model blood was monkey blood with added mouse blood, where the mouse origin DNA was a model for integrated DNA.

Whole blood from a Balb/c mouse was diluted step-wise with a phosphate buffered saline (2.68 mM KCl, 1.47 mM $KH_2PO_4$, 137 mM NaCl, 8.1 mM $Na_2HPO_4$), to obtain solutions which contain $10^4$, $10^3$, $10^2$, 10, and 0 leukocytes in 2 μl of solution.

9 μl aliquot of sodium citrate treated whole monkey blood, which contained 15,000 leukocytes in 1 μl, was dispensed into 0.5 ml microcentrifuge tubes. 2 μl aliquot of the diluted mouse blood solutions were added to the microcentrifuge tubes to produce model monkey blood with different concentrations of the target DNA. The model blood contained $10^4$, $10^3$, $10^2$, 10, or 0 mouse leukocytes.

A Magnetic Particle solution was prepared by diluting a Magnetic particle solution supplied by AMRAD Operations Pty Ltd., under its trademark COLLECTAGENE, fifty one (51) times in a phosphate buffered saline (PBS). 252 μl of this Magnetic Particles-PBS mixture was added to the model blood tubes prepared above. After incubation at room temperature for 10 min., the leukocyte cell conjugated particles were isolated using a magnetic base and the remaining solution was removed by pipette.

The conjugated particles were subjected to PCR without further purification.

The PCR primers and reactions were the same as in Example 1. 100 μl of a reaction mixture for PCR (described below) was added to the leukocyte conjugated particles in the tubes. In order to examine the relationship between pH and the degree of DNA amplification, dual reactions which differed only in the pH of the Tris-HCl buffer were carried out. 1 M Tris buffers pH 8.3 and 9.5 were prepared in the manner described in Example 1.

Reaction Mixture for PCR 10 mM Tris-HCl: one of the two 1 M Tris buffers described above was added to produce a final concentration of 10 mM Tris 1 μM each of primers P1 and P2

1.5 mM $MgCl_2$ 50 mM KCl

200 μM each deoxyribonucleotide (dNTP)i.e., deoxy-adenosine-triphosphate(dATP), deoxy-guanosine-triphosphate(dGTP), deoxy-thymidine-triphosphate (dTTP) and deoxy-cytidine-triphosphate(dCTP)

2.5 units of Taq DNA polymerase (provided by Perkin-Elmer Cetus Instruments under the name of "Ampli Taq")

100 μl of the reaction mixture for PCR was added to the conjugated particles in the tubes. 75 μl of mineral oil was overlaid on the solution in the tubes.

The conditions for thermal cycling and detection by gel electrophoresis were the same as in Example 1.

Figure 3:
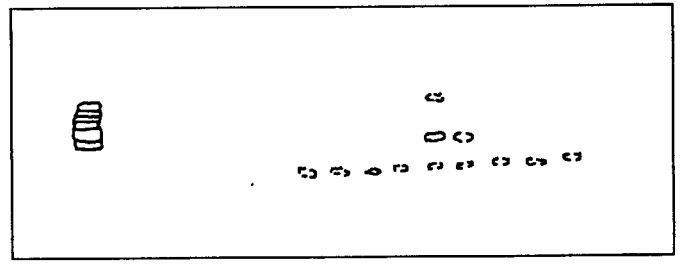
FIG. 3 shows the results of PCR in Example 3 by agarose gel electrophoresis, wherein the PCR was carried out, following pretreatment, with Tris buffers of varying pH and different concentrations of the target DNA.

The results of Example 3 are described in FIG. 3. The letters A and B represent different pH values at which the PCR was carried out, namely:

| Letter | pH |
|---|---|
| A | 8.3 |
| B | 9.5 |

The numbers 1 to 5 represent different concentrations of the mouse leukocytes which include the target DNA, namely:

| Number | Number of mouse leukocytes in the tube |
|---|---|
| 1 | $10^4$ |
| 2 | $10^3$ |
| 3 | $10^2$ |
| 4 | 10 |
| 5 | 0 |

The letter M represents a molecular weight marker which is Hinc II-digested φx174 RF DNA.

No amplification occurred when PCR was carried out with a pH 8.3 buffer, even when the mixture contained $10^4$ leukocytes. This is clear from FIG. 3 which shows that there are no detectable DNA bands in lanes A1, A2, A3, A4 or A5.

However, when PCR was carried out with a pH 9.5 buffer, amplified DNA was detected in lanes B1 and B2. In other words, PCR amplification took place when the concentration of mouse leukocytes was $10^4$ and $10^3$ and a pH 9.5 buffer was used.

---

---

We claim:

1. A process for amplifying a specific nucleic acid sequence comprising the steps of:

a) obtaining a blood sample, which includes a target deoxyribonucleic acid to be amplified;

b) mixing said blood sample with plural primers, a polymerization agent, and mononucleotides, in a buffer solution with a pH between 8.1 to 9.5 as measured at 25° C. to form a reaction mixture; wherein said oligonucleotide primers hybridize to opposite strands of the target deoxyribonucleic acid to be amplified;

c) incubating said reaction mixture under conditions sufficient to release and denature any nucleic acids present;

d) synthesizing an extension product of each primer, wherein the strands to which the primer was hybridized can serve as a template for the synthesis of the extension products thereby forming an extended hybrid;

e) separating the extended hybrid into two single-stranded molecules by heat denaturation;

f) treating the single-stranded molecules generated in step e) with the plural oligonucleotide primers and an excess amount of mononucleotides under conditions such that a second primer extension product is synthesized using each of the single-stranded molecules produced in step e) as a template; and g) repeating the steps e) and f) at least once, wherein said target deoxyribonucleic acid is amplified in the presence of impurities and in the absence of a protein extractive step.

2. The process according to claim 1, wherein said polymerization agent is a thermostable polymerase.

3. The process according to claim 2, wherein said thermostable polymerase is Taq DNA polymerase.

4. The process according to claim 1, wherein said primers are oligodeoxyribonucleotides.

5. The process according to claim 1, wherein said deoxyribonucleic acid to be amplified is a human immunodeficiency virus nucleic acid.

6. The process according to claim 1, wherein said buffer solution includes a pH buffer selected from the group consisting of a 10 mM N-Tris (hydroxymethyl) aminomethane buffer, a 10 mM 2-(Cyclohexylamino) ethanesulfonic acid buffer and a 10 mM 3-N-Cyclohexylamino-2-hydroxypropanesulfonic acid buffer.

7. The method according to claim 1, wherein said impurities are cell membranes and proteins.

8. The process according to claim 1, further comprising collecting leukocytes from said blood sample and using said leukocytes in said process for amplifying a specific nucleic acid sequence.

9. A process for detecting the presence of at least one specific deoxyribonucleic acid sequence in a blood sample, comprising the steps of:
   a) obtaining a blood sample;
   b) mixing the blood sample with plural primers, a polymerization agent, and mononucleotides, in a buffer solution with a pH between 8.1 to 9.5 as measured at 25° C. to form a reaction mixture; wherein said primers hybridize to opposite strands of the deoxyribonucleic acid to be detected;
   c) incubating said reaction mixture under conditions sufficient to release and denature any nucleic acids present;
   d) synthesizing an extension product of each oligonucleotide primer, wherein the strands to which the oligonucleotide primer was hybridized can serve as a template for the synthesis of the extension products thereby forming an extended hybrid;
   e) separating the extended hybrid into two single-stranded molecules by heat denaturation;
   f) treating the single-stranded molecules generated in step e) with the plural oligonucleotide primers and a molar excess of mononucleotides under conditions such that a second primer extension product is synthesized using each of the single-stranded molecules produced in step e) as a template;
   g) repeating the steps e) and f) at least once; and
   h) detecting any nucleic acids produced in steps b)–g) as an indication of the presence of the specific deoxyribonucleic acid sequence to be detected, wherein said specific deoxyribonucleic acid sequence is detected in the presence of impurities and in the absence of a protein extractive step.

10. The process according to claim 9, wherein said deoxyribonucleic acids are detected using gel electrophoresis.

11. The process according to claim 9, wherein said deoxyribonucleic acid sequence to be detected is a retroviral nucleic acid sequence.

12. The process according to claim 11, wherein said deoxyribonucleic acid sequence to be detected is a human immunodeficiency virus (HIV) nucleic acid sequence.

13. The process according to claim 9, further comprising collecting leukocytes from said blood sample and using said leukocytes in said process for detecting the presence or absence of at least one specific deoxyribonucleic acid sequence.

14. In a process for amplifying a specific deoxyribonucleic acid sequence using polymerase chain reaction, an improvement comprising mixing a blood sample with plural primers, a polymerization agent, and mononucleotides, in a buffer solution with a pH between 8.1 to 9.5 as measured at 25° C. to form a reaction mixture, wherein said specific deoxyribonucleic acid sequence is amplified in the presence of impurities and in the absence of a protein extractive step.

15. In a process for detecting the presence of at least one specific deoxyribonucleic acid sequence in a blood sample using polymerase chain reaction, an improvement comprising mixing a blood sample with plural primers, a polymerization agent, and mononucleotides, in a buffer solution with a pH between 8.1 to 9.5 as measured at 25° C. to form a reaction mixture, wherein said specific deoxyribonucleic acid sequence is detected in the presence of impurities and in the absence of a protein extractive step.

16. In a reaction kit for detecting the presence or absence of at least one specific deoxyribonucleic acid sequence in a blood sample using polymerase chain reaction, an improvement comprising a reaction buffer solution with a pH value between 8.1 to 9.5 at 25° C.

17. A process for amplifying a specific nucleic acid sequence comprising the steps of:
   a) obtaining a blood sample, which includes a target deoxyribonucleic acid to be amplified;
   b) lysing any erythrocytes in said sample;
   c) mixing said blood sample with plural primers, a polymerization agent, and mononucleotides, in a buffer solution with a pH between 8.1 to 9.5 as measured at 25° C. to form a reaction mixture; wherein said oligonucleotide primers hybridize to opposite strands of the target deoxyribonucleic acid to be amplified;
   d) incubating said reaction mixture under conditions sufficient to release and denature any nucleic acids present;
   e) synthesizing an extension product of each primer, wherein the strands to which the primer was hybridized can serve as a template for the synthesis of the extension products thereby forming an extended hybrid;
   f) separating the extended hybrid into two single-stranded molecules by heat denaturation;
   g) treating the single-stranded molecules generated in step f) with the plural oligonucleotide primers and an excess amount of mononucleotides under conditions such that a second primer extension product is synthesized using each of the single-stranded molecules produced in step f) as a template; and
   h) repeating the steps f) and g) at least once, wherein said target deoxyribonucleic acid is amplified in the presence of impurities and in the absence of a protein extractive step.

18. A process for detecting the presence of at least one specific deoxyribonucleic acid sequence in a blood sample, comprising the steps of:
   a) obtaining a blood sample;
   b) lysing any erythrocytes in said sample;
   c) mixing the blood sample with plural primers, a polymerization agent, and mononucleotides, in a buffer solution with a pH between 8.1 to 9.5 as measured at 25° C. to form a reaction mixture; wherein said primers hybridize to opposite strands of the deoxyribonucleic acid to be detected;
   d) incubating said reaction mixture under conditions sufficient to release and denature any nucleic acids present;
   e) synthesizing an extension product of each oligonucleotide primer, wherein the strands to which the oligonucleotide primer was hybridized can serve as a template for the synthesis of the extension products thereby forming an extended hybrid;
   f) separating the extended hybrid into two single-stranded molecules by heat denaturation;
   g) treating the single-stranded molecules generated in step f) with the plural oligonucleotide primers and a molar excess of mononucleotides under conditions such that a second primer extension product is synthesized using each of the single-stranded molecules produced in step f) as a template;

h) repeating the steps f) and g) at least once; and i) detecting any nucleic acids produced in steps c)–h) as an indication of the presence of the specific deoxyribonucleic acid sequence to be detected, wherein said specific deoxyribonucleic acid sequence is detected in the presence of impurities and in the absence of a protein extractive step.

19. A reaction kit for detecting the presence or absence of at least one specific deoxyribonucleic acid sequence in a blood sample using PCR, comprising the following components:

a) two oligonucleotide primers, wherein said primers are complementary to target sites of the specific nucleic acid sequence to be detected, b) a polymerization agent, c) nucleoside triphosphates, and d) a buffer solution with a pH value between 8.1 to 9.5 at 25° C.

20. The kit according to claim 19, wherein said polymerization agent is a thermostable polymerase.

21. The kit according to claim 19, wherein said polymerization agent is a DNA polymerase and said oligonucleotide primers are oligodeoxyribonucleotides.

22. The kit according to claim 19, further comprising a reverse transcriptase.

* * * * *